Aug. 26, 1947. J. L. LEGENDRE Plant Pat. 756
PHLOX PLANT
Filed Sept. 18, 1946
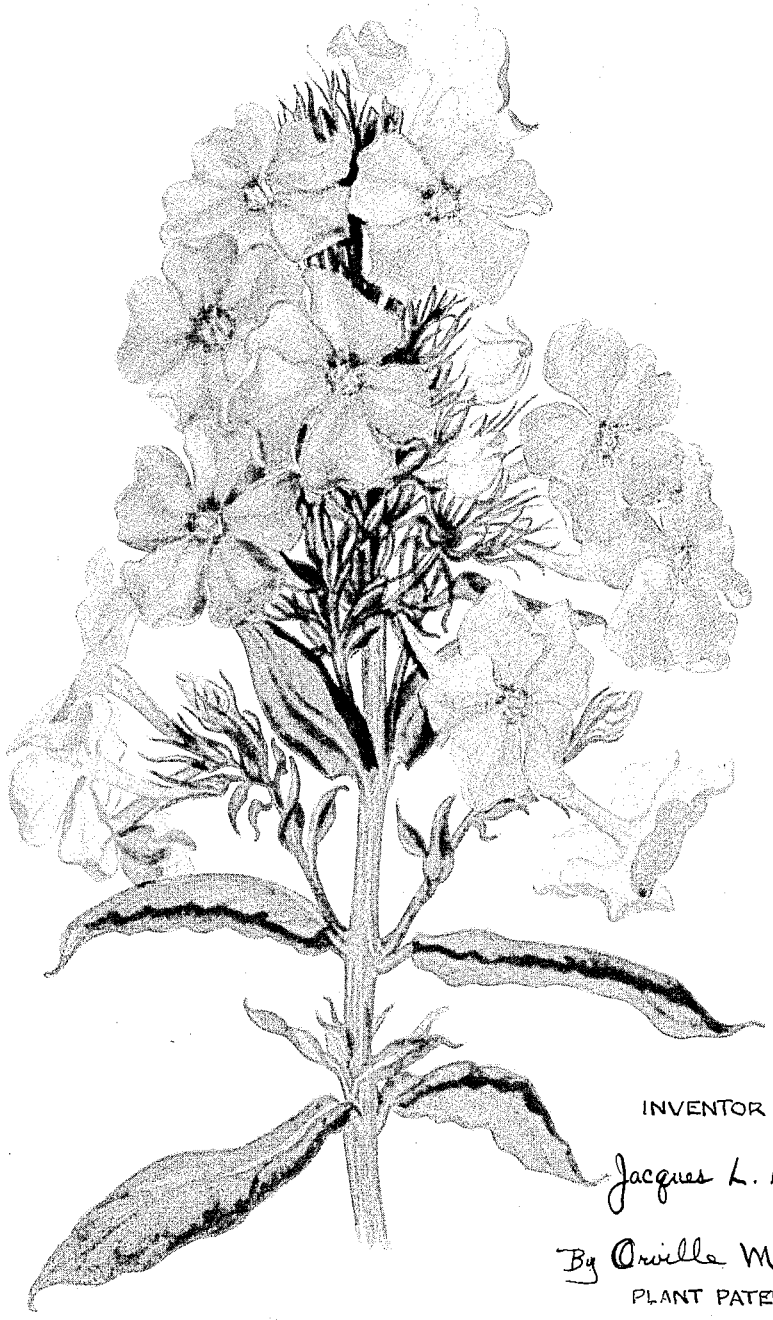
INVENTOR
Jacques L. Legendre
By Orville M. Kile
PLANT PATENT AGENT Patented Aug. 26, 1947

Plant Pat. 756

UNITED STATES PATENT OFFICE

756

PHLOX PLANT

Jacques L. Legendre, Wachapreague, Va.

Application September 18, 1946, Serial No. 697,696

1 Claim. (Cl. 47—60)

My present invention relates to a new variety of hardy phlox of the genus Decussata. It has a distinct new color for this type of phlox and although dwarf and compact in growth has large trusses with exceedingly large individual flowers. It is exceptionally resistant to disease and produces an abundance of flowers over a long blooming season.

My new variety is more like the variety Jules Sandeau than any other variety known to me but my variety differs from it in many respects, particularly in larger size of truss and floret, greater compactness of growth, greater resistance to disease, and difference of floret color, especially of the reverse of the petals.

My variety originated as the result of a cross made by me between the variety Eva Feerster and an unnamed seedling produced at a nursery in Wachapreague. It has been asexually reproduced by me and its characteristics have proved to be firmly fixed.

The accompanying illustration shows a truss or head of my new phlox in approximately its true colors. This head had been shipped to the artist and many of the florets had been knocked off in transit. However, it serves to show the colors and form of the inflorescence and its relation to the stalk, as well as the stems and foliage and the production of many lateral flower stems.

In the following detailed description of my new variety, color plate references indicate Ridgway's Color Standards and Nomenclature. Where no plate reference is given, the ordinary dictionary meaning is intended.

*The plant*

Growth habit: Herbaceous. Very vigorous in growth and prolific in production.

Form: Dwarf, compact and bushlike, usually growing to about a foot in height. Stalks grow singly from the ground but branch a great deal, thus providing many lateral stems for additional flower heads.

Root growth: Large, spreading and vigorous root growth, providing an excellent foundation for plant growth.

Blooming habit: Very prolific bloomer, producing many flowers continuously from June to October. Many lateral flower heads are formed.

Health: Very healthy and resistant to disease and adverse weather conditions.

Stalks: Tough and strong. Inclined to be stiff, upright and heavy. Lighter green than the foliage and with occasional reddish tinge. Internodes short.

Foliage: More abundant than usually found on this type of phlox, and the leaves are larger.

Leaves appear opposite in pairs and new flower branches usually emerge from the axils of both leaves of the pair. Color of leaves is approximately Spinach Green (Plate V) on the upper surface and somewhat lighter on the under surface. They are broadly lanceolate in shape and the edges usually roll under slightly.

*The flower*

Inflorescence: Compound truss or head, consisting of many florets borne on small pedicels. The shape of the truss varies but is usually elongated.

Bud: When the buds are still tightly furled they are long and pointed and silvery white with green tracings. As they begin to unfurl like miniature sunshades they have a pink tone and begin to show some of the darker color of their inner surface which gradually becomes the predominating color.

Flower:

*Size.*—Individual florets are very large, measuring as much as 1⅝ inches in diameter.

*Color.*—With the exception of a light eye, the entire upper surface is a bright clear new color which approximates Rhodamine Purple (Plate XII). The reverse side is a translucent silvery white through which the upper surface color shines, giving the effect of silvery pink.

*Shape.*—The lower part of the flower is a long slender tube an inch or more in length, which separates into five large lobes or petals which lie relatively flat but curl slightly. Petals are frequently overlapping.

*Substance.*—Petals are of heavy substance.

*Permanence.*—Flowers last exceedingly well on the plant and are not affected by adverse weather conditions, but they do not last well when cut.

*Calyx.*—Very foliaceous, producing the effect of very fine foliage on the truss, particularly where florets have dropped.

Having thus disclosed my invention, I claim:

The new and distinct variety of phlox plant, substantially as herein shown and described, characterized particularly by its exceptional resistance to disease; its strong compact growth; its prolific blooming habit; its production of many lateral flower stems; its long blooming season; and its large trusses of very large individual florets having the novel color combination of bright Rhodamine Purple on the upper surface and silvery pink on the under surface.

JACQUES L. LEGENDRE.